United States Patent [19]

Butterfield et al.

[11] Patent Number: 5,617,867
[45] Date of Patent: Apr. 8, 1997

[54] TONOMETER MOUNTING DEVICE

[75] Inventors: Robert D. Butterfield, Poway; Charles R. Holdaway; Stephen A. Martin, both of San Diego; Stanley J. Boyer, Carlsbad; Christine A. Giurdanella-Renzi, San Diego, all of Calif.

[73] Assignee: IVAC Medical Systems, Inc., San Diego, Calif.

[21] Appl. No.: 344,252

[22] Filed: Nov. 23, 1994

[51] Int. Cl.⁶ .................................................. A61B 5/00
[52] U.S. Cl. .................. 128/672; 128/687; 128/690; 128/748
[58] Field of Search ............ 73/862.581, 862.621, 73/862.626, 862.627, 862.632, 862.68, DIG. 4; 128/748, 666, 667, 668, 672, 677, 680–3, 686, 687–690, 661.08, 660.02, 645, 646, 691–694, 739, 740, 774–782

[56] References Cited

U.S. PATENT DOCUMENTS

| | | | |
|---|---|---|---|
| 3,090,377 | 5/1963 | Salisbury et al. | 128/677 |
| 3,099,262 | 7/1963 | Bigliano | 128/672 |
| 4,185,641 | 1/1980 | Minior et al. | 128/675 |
| 4,237,935 | 12/1980 | Delmonte et al. | 128/675 |
| 4,353,374 | 10/1982 | Rebbe et al. | 128/686 |
| 4,406,289 | 9/1983 | Wesseling et al. | 128/672 |
| 4,429,700 | 2/1984 | Thees et al. | 128/681 |
| 4,901,733 | 2/1990 | Kaida et al. | 128/672 |
| 4,993,422 | 2/1991 | Hon et al. | 128/672 |
| 5,240,007 | 8/1993 | Pytel et al. | 128/672 |
| 5,263,484 | 11/1993 | Martin et al. | 128/672 |
| 5,271,405 | 12/1993 | Boyer et al. | 128/672 |

FOREIGN PATENT DOCUMENTS

| | | | |
|---|---|---|---|
| 9002512 | 3/1990 | WIPO | 128/672 |
| 9220275 | 11/1992 | WIPO | 128/672 |

*Primary Examiner*—Angela D. Sykes
*Assistant Examiner*—Robert L. Nasser, Jr.
*Attorney, Agent, or Firm*—Fulwider Patton Lee & Utecht, LLP

[57] ABSTRACT

A device for mounting a tonometry sensor upon a patient's wrist includes a base portion that is specifically adapted to generally conform to the patient's wrist while providing a stable placement of the tonometry sensor relative to a preselected artery. A sensor housing is movably mounted upon the base portion and configured such that the mounting device has an essentially equal thickness at each end of the device. A strap member is provided for releasably securing the mounting device to a patient's wrist. The mounting device facilitates more accurate, non-invasive blood pressure measurement by providing a stable placement of the tonometry sensor relative to the tissue overlying a preselected artery at a measurement location and, further, limits undesirable movement by the patient to thereby reduce undesirable error in the blood pressure measurement.

22 Claims, 2 Drawing Sheets

5,617,867

TONOMETER MOUNTING DEVICE

BACKGROUND OF THE INVENTION

This invention relates generally to a mounting device for use in a non-invasive tonometry system. More particularly, this invention relates to a wrist mount device for use in non-invasively monitoring a patient's blood pressure while providing stability to the placement of the tonometry sensor relative to the patient's anatomy.

Routine methods of monitoring a patient's blood pressure include the widely used auscultatory method known as the Korotkoff method. This method is non-invasive, however, it only provides a measurement of systolic and diastolic pressure on an intermittent basis; it does not provide the entire waveform on a continuous basis. Furthermore, the use of the Korotkoff method often yields inaccurate results. Moreover, the rate at which blood pressure can be recorded is limited by the inflation and deflation rate of the occlusive cuff. Therefore, true beat-to-beat continuous blood pressure monitoring is not possible using this method.

Other methods include the use of intra-arterial catheters that are invasively inserted within a patient's artery. Although such invasive methods often yield accurate results, the potential trauma to a patient often outweighs the benefits of using such a method. Further, invasive tonometry methods are cumbersome in that sterilization of the various apparatus used in conjunction with the invasive catheter is often difficult to maintain. Further, a significant risk in using an invasive method of monitoring blood pressure includes the possibility of introducing air bubbles into the patient's blood stream.

Recent developments in tonometry include the development of non-invasive tonometry sensors that monitor the blood pressure waveform as a function of tissue stress in the tissue overlying an artery of interest. One example of such a sensor is disclosed in U.S. Pat. No. 5,158,091. With the advent of such non-invasive sensors, continuous, accurate blood pressure measurements have become possible. In order to achieve accurate blood pressure measurement utilizing such a non-invasive tissue stress sensor, however, it becomes necessary to ensure that the sensor is maintained in proper communication with the tissue overlying the artery of interest. For example, it is necessary that the tissue stress sensor be maintained in controlled contact with the overlying tissue such that unnecessary relative movements between the tissue and the sensor do not introduce undesirable error or artifacts into the blood pressure measurement.

It is therefore necessary and desirable to provide a device that maintains a tissue stress sensor in proper communication with the overlying tissue in a predictable fashion. Moreover, it is important that a patient be restricted from unnecessary movement of that portion of the anatomy where the tissue stress sensor is located in order to avoid a misplacement of the sensor relative to the artery of interest. It is also important to provide a mounting device for the tissue stress sensor that takes into consideration patient comfort and economics of use. Further, it is desirable to provide a device for mounting a tissue stress sensor on a selected portion of a patient's anatomy that is readily usable on a variety of patients.

SUMMARY OF THE INVENTION

In general terms, this invention provides a mounting device for mounting a non-invasive tonometry sensor adjacent a preselected artery in a patient's wrist. The mounting device includes a base portion that has an essentially planar outward face and a generally arcuate inward face. The outward face is characterized by a specific length and width. The inward face is adapted to generally conform to the anterior and medial side of a patient's wrist. The inward face is characterized by an arcuate length that is greater than the length of the outward face. The base portion has a thickness that is defined by a distance between the outward and inward faces. The thickness of the base portion is substantially greater at a second end of the base portion, which is located toward the medial side of the patient's wrist when the mounting device is properly placed upon the wrist. The mounting base portion also has two windows near a first end of the base portion that is opposite from the second end just mentioned. The mounting device also includes a sensor housing that is movably attached to the base portion such that the sensor, which is near one end of the sensor housing, is selectively positionable in one of the windows. The sensor is thereby put into operative communication with the tissue overlying the preselected artery through the selected window. The mounting device has a combined thickness that is defined by the base portion thickness and a height of the sensor housing. The combined thickness of the mounting device is essentially equal near the first and second ends of the base portion. Having an equal combined thickness at each end of the mounting device facilitates a stable placement of the tonometry sensor relative to the preselected artery. Lastly, a strap member is provided for releasably securing the base portion about the patient's wrist in a preselected position.

Further details and advantages associated with this invention will become apparent to those skilled in the art from the following detailed description of the preferred embodiments.

DETAILED DESCRIPTION OF THE PREFERRED EMBODIMENTS

Figure 1:
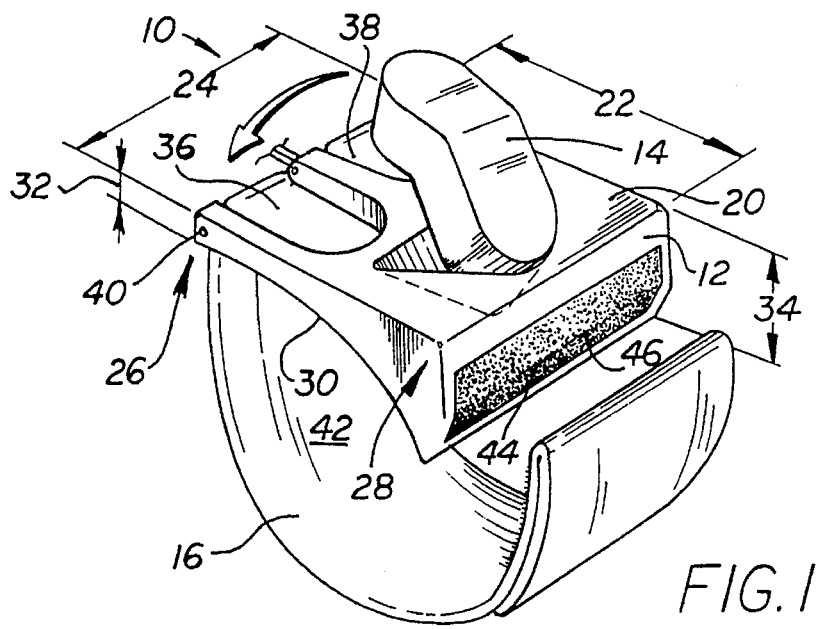
FIG. 1 is a perspective view of a tonometer mounting device designed in accordance with this invention.

FIG. 1 is a perspective view of a mounting device 10 designed in accordance with this invention. Mounting device 10 includes base portion 12, sensor housing 14 and strap member 16. Base portion 12 includes outward surface 20, which is generally planar. Outward surface 20 has a length 22 and a width 24. Length 22 is defined between a first end 26 and a second end 28 of base portion 12. Inward surface 30 is generally arcuate and adapted to generally conform to a patient's wrist when base portion 12 is properly mounted upon a patient's wrist. Inward surface 30 has a length that is substantially greater than length 22 of outward surface 20. Base portion 12 has a thickness defined by a distance between outward surface 20 and inward surface 30. As can be appreciated from FIG. 1, a thickness 32 near the first end 26 of base portion 12 is substantially smaller than thickness 34 near the second end 28 of base portion 12.

Base portion 12 includes first window 36 and second window 38, through which a patient's tissue is left exposed to facilitate blood pressure measurement as will be more fully described below. Windows 36 and 38 are located at first end 26 of base portion 12.

Pin 40 is provided through first end 26 of base portion 12 to facilitate coupling mounting strap member 16 to base portion 12. As can be appreciated from the drawings, a loop or opening is provided through an end of strap member 16 that receives pin 40 such that strap member 16 can rotate about pin 40. Strap member 16 is preferably made of a fabric material that is lightweight and flexible. A material for strap member 16 is also preferably washable and durable in order to withstand repeated use on a variety of patients. Strap member 16 has an inside face 42 that is received about a patient's wrist when mounting device 10 is placed upon a patient's wrist. The inside of strap member 16 is releasably coupled to a gripping surface 44 located at second end 28 of base portion 12.

Figure 2:
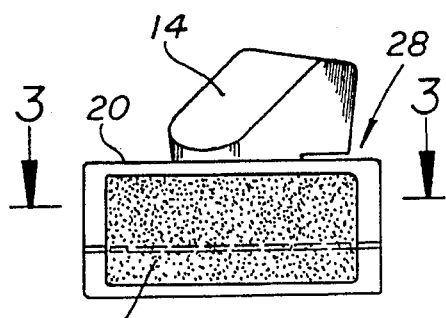
FIG. 2 is a planar view of selected portions of the mounting device of FIG. 1.
Figure 3:
FIG. 3 is a cross-sectional view taken in a plane of FIG. 2.

Gripping surface 44 preferably includes a matrix of nylon teeth 46 that grippingly engage a fabric on the inside 42 of strap member 16. The gripping surface 44 and the inside 42 of strap member 16 in the preferred embodiment are commonly known as a VELCRO™ strap and connector. FIGS. 2 and 3 show, in more detail, the nylon teeth 46 of gripping surface 44. Other fastening or gripping means may be provided near second end 28 of base portion 12, however, a VELCRO™ strap is generally preferred because of its durability and the common ease of use associated with a VELCRO™ strap. For example, a VELCRO™ strap is readily secured and/or released from a patient's wrist. Further, a VELCRO™ strap provides an essentially infinitely variable adjustability to strap member 16 such that mounting device 10 is readily adapted to be worn on a variety of patients having wrists that differ in size.

Figure 5:
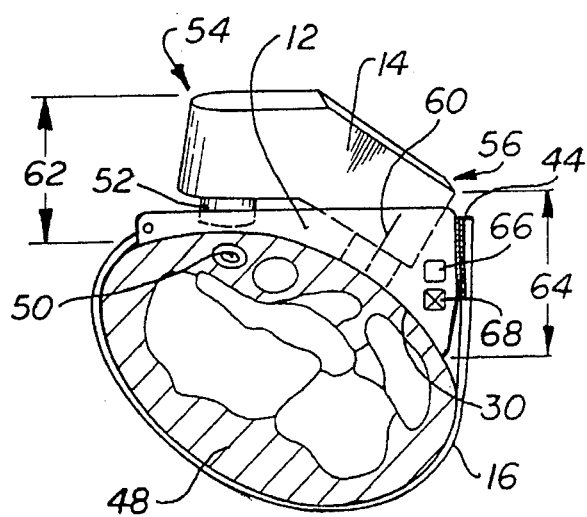
FIG. 5 is a side planar view of the mounting device of FIG. 4 illustrated mounted upon a patient's wrist, which is shown in cross section.
Figure 4:
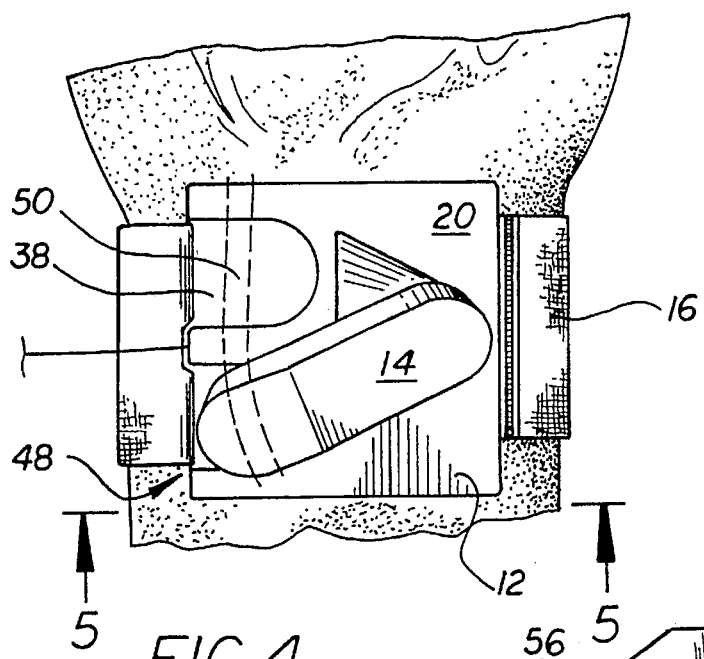
FIG. 4 is a top planar view illustrating the mounting device of FIG. 1 mounted upon the left wrist of a patient.
Figure 6:
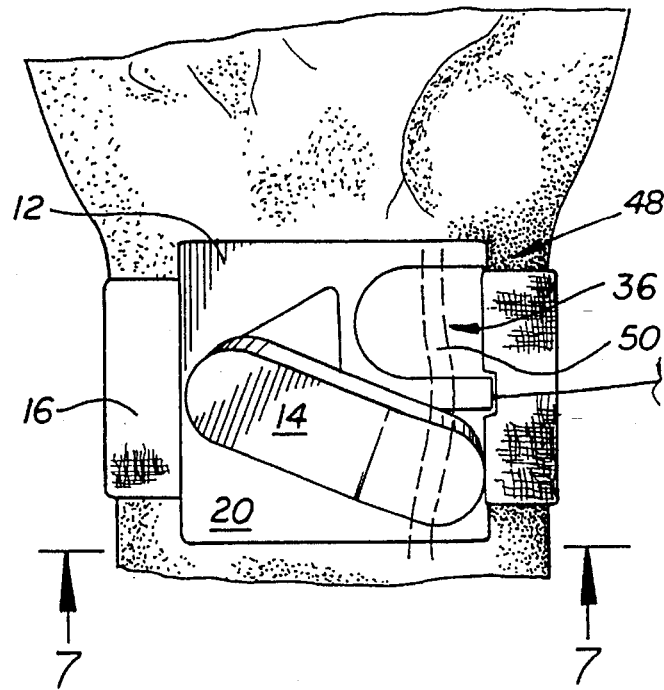
FIG. 6 is a top planar view of the mounting device of FIG. 1 mounted upon the right wrist of a patient.

FIGS. 4–7 generally illustrate how mounting device 10 is secured about a patient's wrist 48. Typically, blood pressure measurements are taken in a non-invasive tonometry system from the radial artery 50 located in the wrist of a patient. Mounting device 10 includes first window 36 and second window 38, which render mounting device 10 readily adaptable to the right wrist (as shown in FIG. 6) or the left wrist (as shown in FIG. 4) of a patient. Sensor housing 14 is preferably pivotally mounted to base portion 12 such that sensor 52 can be positioned above window 36 or 38. Sensor 52 is located at first end 54 of sensor housing 14. Second end 56 of sensor housing 14 is pivotally mounted upon base portion 12. Sensor housing 14 pivots about pivot axis 60.

Pivot axis 60 is preferably located centrally on base portion 12 and closer to second end 28 of base portion 12. The central location of pivot axis 60 (central being between the top and bottom of base portion 12 as illustrated in FIGS. 4 and 5) enhances a stable placement of mounting device 10 upon the wrist of a patient because the distribution of weight of the various components of mounting device 10 is balanced. An equal distribution of weight and balance is preferred because that facilitates a more stable placement of mounting device 10 about the wrist of a patient. As generally discussed above, a stable and predictable mounting of a tonometry sensor relative to a preselected artery is important in order to avoid the introduction of undesirable error or artifacts into a blood pressure measurement.

As illustrated in FIG. 5, mounting device 10 has a combined thickness 62 near first end 26 of base portion 12. Mounting device 10 also has a combined thickness 64 near second end 28 of base portion 12. In the preferred embodiment, combined thicknesses 62 and 64 are essentially equal. Having an essentially equal thickness or cross-sectional area at each end of mounting device 10 further facilitates a stable placement of mounting device 10 upon the wrist of a patient.

Mounting device 10 is used in the following general manner. First, the tissue on a patient's wrist is palpated by a medical professional in order to generally locate radial artery 50. Mounting base 12 is then placed upon the patient's wrist such that radial artery 50 and the overlying tissue is located within window 36 or 38. In the case of placing mounting device 10 upon the left wrist of a patient, it is probably preferable, due to the normal anatomical structure of a person's wrist, that window 38 be located above the point of greatest surface pulse in the tissue overlying the radial artery 50. While holding mounting base 12 upon the patient's wrist, strap member 16 is wrapped about the wrist and securely fastened by using gripping surface 44. The medical professional can then palpate the patient's wrist through window 38 when sensor housing 14 is pivoted such that window 38 is exposed, as illustrated in FIG. 4. If palpation of the tissue under window 38 does not reveal an adequate surface pulse, mounting device 10 can be repositioned upon the patient's wrist until a sufficient pulse is available through window 38. Once a desirable position of mounting device 10 is found upon wrist 48, sensor housing 14 is pivoted relative to base portion 12 such that sensor 52 is located above window 38.

Figure 7:
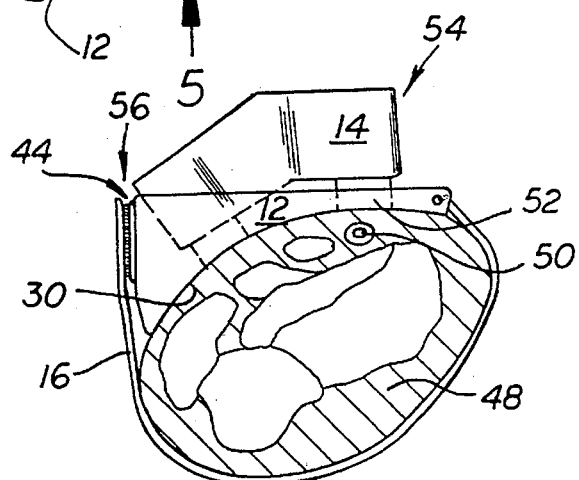
FIG. 7 is an illustration of the embodiment of FIG. 6 with the tonometry sensor in operative communication with the tissue overlying the preselected artery.

Referring now to FIGS. 5 and 7, sensor 52 is projected outward from sensor housing 14 until sensor 52 comes into contact with the tissue overlying radial artery 50. Sensor 52 is moved against the overlying tissue until radial artery 50 is applanated to a desired state and blood pressure measurement is then possible. The specific apparatus for moving sensor 52 relative to sensor housing 14 and radial artery 50 and methodology for applanating a preselected artery are not the subject of this invention and, therefore, will not be further described herein.

A significant advantage provided by this invention is a stable placement of sensor 52 relative to radial artery 50. As discussed above, the combined thicknesses 62 and 64 are preferably generally equal in order to provide a balancing effect in placing mounting device 10 upon the patient's wrist. An equal distribution of weight facilitates a stable placement of mounting device 10 upon the patient's wrist. Further, as discussed above, sensor housing 14 preferably pivots about a pivot axis 60, which is located centrally on base portion 12 in order to further enhance an equal distribution of weight. In order to render the mounting device 10 adaptable to a variety of sensors 52, base portion 12 includes openings or slots 66 that are adapted to receive weights 68. Weights 68 can be selectively provided in base portion 12 in order to provide further counter balancing or an equal distribution of weight depending on the weight of sensor 52.

Mounting device 10 further enhances accurate blood pressure measurement because of the shape of base portion 12. Inward surface 30 is, as illustrated, adapted to generally conform to a patient's wrist on the anterior and medial sides of the wrist. Further, width 24 of base portion 12 is preferably large enough such that when mounting device 10 is secured about a patient's wrist, relative movements between the radial and ulnar joints and the carpal bones of the wrist are restricted. In other words, when mounting device 10 is secured about a patient's wrist, relative movements between bones within the patient's arm and wrist are restricted, thereby limiting the patient's ability to move the hand relative to the wrist. This limited movement is preferred because it enhances a predictable and stable positioning of sensor 52 relative to the tissue overlying radial artery 50. Undesirable movements by a patient can cause sensor 52 to be misplaced away from an optimal position relative to radial artery 50. Further, undesirable movements can introduce noise and other artifacts into a blood pressure measurement when using a non-invasive tissue stress sensor such as that disclosed in U.S. Pat. No. 5,158,091. Therefore, this invention provides a mounting device for a non-invasive tonometry sensor that enhances accurate blood pressure measurement because of the stable placement of the tissue stress sensor relative to the patient's anatomy and, more particularly to a preselected artery. Further, this invention provides a device that restrains a patient from introducing undesirable error into blood pressure measurement through undesirable movements of those portions of the anatomy close to the monitoring site.

The preceding description is exemplary rather than limiting in nature. Variations and modifications will become apparent to those skilled in the art that do not depart from the purview and spirit of this invention. The scope of this invention is to be limited only by the appended claims and all fair, legal equivalents thereof.

What is claimed is:

1. A mounting device for mounting a non-invasive tonometry sensor adjacent a preselected artery in a patient's wrist, comprising:

a base portion having an essentially planar outward face and a generally arcuate inward face, said outward face having a length and a width, said inward face being adapted to generally conform to an anterior side of the patient's wrist and having an arcuate length that is greater than said outward face length, said base portion having a thickness defined by a distance between said outward and inward faces, said base portion having two windows near a first end of said base portion, said thickness being substantially greater at a second end of said base portion distal from said windows;

a sensor housing having the tonometry sensor near one end of said housing, said housing being movably attached to said base portion such that said sensor is selectively positionable in one of said windows and thereby adapted to be put into operative communication with tissue overlying the preselected artery;

said mounting device having a combined thickness defined by said base portion thickness and a height of said sensor housing, said combined thickness being essentially equal near said first and second ends of said base portion to thereby facilitate a stable placement of the sensor relative to the preselected artery, and said sensor housing and said base portion having a combined distribution of weight that is essentially equal at said first and second ends of said base portion, respectively, to thereby further facilitate said stable placement of the sensor relative to the preselected artery; and a strap member for releasably securing said base portion about the patient's wrist in a preselected position.

2. The mounting device of claim 1, wherein said base portion width is large enough such that when said device is secured about the patient's wrist relative movement between bones within the patient's arm and wrist is restricted to thereby facilitate maintaining the sensor in a preselected position relative to the preselected artery to thereby reduce undesirable error and artifacts when monitoring blood pressure within the preselected artery.

3. The mounting device of claim 1, wherein said strap member has a width substantially equal to said width of said outward face.

4. The mounting device of claim 3, wherein said strap member is selectively releasably attached to said second end of said base portion.

5. The mounting device of claim 1, wherein said sensor housing is pivotally mounted onto said base portion.

6. The mounting device of claim 5, wherein said sensor housing pivots about an axis that is essentially centered on said base portion proximate said second end of said base portion to thereby further facilitate said stable placement of the sensor relative to the preselected artery.

7. A mounting device for mounting a non-invasive tonometry sensor adjacent a preselected artery in a patient's wrist, comprising:

a base portion having an essentially planar outward face and a generally arcuate inward face, said outward face having a length and a width, said inward face being adapted to generally conform to an anterior side of the patient's wrist and having an arcuate length that is greater than said outward face length, said base portion having a thickness defined by a distance between said outward and inward faces, said base portion having two windows near a first end of said base portion, said thickness being substantially greater at a second end of said base portion distal from said windows;

a sensor housing having the tonometry sensor near one end of said housing, said housing being movably attached to said base portion such that said sensor is selectively positionable in one of said windows and thereby adapted to be put into operative communication with tissue overlying the preselected artery;

said mounting device having a combined thickness defined by said base portion thickness and a height of said sensor housing, said combined thickness being essentially equal near said first and second ends of said base portion to thereby facilitate a stable placement of the sensor relative to the preselected artery, wherein said base portion second end has a weight receiving portion for receiving a weight to selectively vary a mass of said base portion second end to thereby further facilitate said stable placement of the sensor relative to the preselected artery; and a strap member for releasably securing said base portion about the patient's wrist in a preselected position.

8. The mounting device of claim 7, wherein said base portion width is large enough such that when said device is secured about the patient's wrist, relative movement between bones within the patient's arm and wrist is restricted to thereby facilitate maintaining the sensor in a preselected position relative to the preselected artery to thereby reduce undesirable errors and artifacts when monitoring blood pressure within the preselected artery.

9. The mounting device of claim 7, wherein said strap member has a width substantially equal to said width of said outward face.

10. The mounting device of claim 9, wherein said strap member is selectively releasably attached to said second end of said base portion.

11. The mounting device of claim 7, wherein said sensor housing is pivotally mounted onto said base portion.

12. The mounting device of claim 11, wherein said sensor housing pivots about an axis that is essentially centered on said base portion proximate said second end of said base portion to thereby further facilitate said stable placement of the sensor relative to the preselected artery.

13. A mounting and restraint device for mounting a tonometry sensor relative to a preselected artery within a patient's wrist and for restraining the patient's wrist from undesirable movement that may tend to introduce error into blood pressure measurement, comprising:

- a base portion having an essentially constant width between first and second ends and adapted to generally conform to the patient's wrist with the width lying along a direction generally perpendicular to the patient's arm, said width being wide enough to restrict relative movement between bones within the patient's arm and wrist when said base portion is securely placed on the patient's wrist, said base portion having a nominal thickness near said first end and a greatest thickness near said second end, said base portion having two windows proximate said first end for enabling said base portion to be worn on a left or right wrist;
- a sensor housing pivotally connected to said base portion and adapted for housing the tonometry sensor proximate a first housing end, said housing pivoting about a centrally located pivot axis proximate said base second end such that the sensor operatively engages tissue overlying the preselected artery through one of said windows, said pivot axis being proximate a second housing end distal from the tonometry sensor; and
- a band coupled to said first end of said base portion and releasably engaging said second end of said base portion for releasably securing said device about the patient's wrist;
- wherein said sensor housing and said base portion have a combined distribution of weight that is essentially equal at said first and second ends of said base portion, respectively.

14. The device of claim 13, wherein said band has a width substantially equal to said width of said base portion.

15. The device of claim 13, wherein said base portion has a generally planar outward face and a generally arcuate inward face, said inward face being adapted to generally conform to an anterior side of the patient's wrist.

16. The device of claim 15, wherein said second end of said base portion is adapted to be received on a lateral side of the patient's wrist such that said inward face extends across a portion of said anterior and lateral sides, respectively.

17. The device of claim 13, wherein said base portion and said sensor housing have a combined thickness that is essentially equal near said first and second ends.

18. A mounting and restraint device for mounting a tonometry sensor relative to a preselected artery within a patient's wrist and for restraining the patient's wrist from undesirable movement that may tend to introduce error into blood pressure measurement, comprising:

- a base portion having an essentially constant width between first and second ends and adapted to generally conform to the patient's wrist with the width lying along a direction generally perpendicular to the patient's arm, said width being wide enough to restrict relative movement between bones within the patient's arm and wrist when said base portion is securely placed on the patient's wrist, said base portion having a nominal thickness near said first end and a greatest thickness near said second end, said base portion having two windows proximate said first end for enabling said base portion to be worn on a left or right wrist;
- a sensor housing pivotally connected to said base portion and housing a tonometry sensor proximate a first housing end, said housing pivoting about a centrally located pivot axis proximate said base second end such that the sensor operatively engages tissue overlying the preselected artery through one of said windows, said pivot axis being proximate a second housing end distal from the tonometry sensor; and
- a band coupled to said first end of said base portion and releasable engaging said second end of said base portion for releasably securing said device about the patient's wrist;
- wherein said base portion second end has a weight receiving portion for receiving a weight to selectively vary a mass of said base portion second end.

19. The device of claim 18, wherein said band has a width substantially equal to said width of said base portion.

20. The device of claim 18, wherein said base portion has a generally planar outward face and a generally arcuate inward face, said inward face being adapted to generally conform to an anterior side of the patient's wrist.

21. The device of claim 20, wherein said second end of said base portion is adapted to be received on a lateral side of the patient's wrist such that said inward face extends across a portion of said anterior and lateral sides, respectively.

22. The device of claim 18, wherein said base portion and said sensor housing have a combined thickness that is essentially equal near said first and second ends.

* * * * *